United States Patent [19]
Umbreit et al.

[11] Patent Number: 5,872,141
[45] Date of Patent: Feb. 16, 1999

[54] METHOD OF INHIBITING CHOLESTEROL TRANSPORT

[76] Inventors: Jay N. Umbreit, 7175 Bay Rd., Mobile, Ala. 36605; Marcel E. Conrad, 1314 Dauphin St., Mobile, Ala. 36604

[21] Appl. No.: 801,319

[22] Filed: Feb. 18, 1997

[51] Int. Cl.[6] ................................................ A61K 31/425
[52] U.S. Cl. ........................................................ 514/368
[58] Field of Search .............................................. 514/368

[56] References Cited

U.S. PATENT DOCUMENTS 5,434,067  7/1995  Michaelis et al. ........................ 435/196

OTHER PUBLICATIONS

Brasitus, T.A., et al., J Biol Chem 263:8592–8597 (1988).
Christensen, N.J., et al., J Lipid Res 24:1229–1242 (1983).
Schwender, C.F., et al., Biochem Pharmacol 30:217–222 (1981).
Schwender, C.F., et al., J Med Chem 25:742–745 (1982).
Tebib, K., et al., Enzymes & Proteins 48:51–60 (1995).
Thomson, A.B.R., J Lipid Res 21:1097–1107 (1980).
Thurnhofer, H. & Hauser, H., Biochem 29:2142–2148 (1990).
Thurnhofer, H., et al., Biochima et Biophysica Acta 1064:275–286 (1991).
Tso, P., Adv Lipid Res 21:143–186 (1985).
Van Belle, H., Clin Chem 22:972–976 (1976).
Wauwe, J.V. & Janssen, P.A., Int J Immunopharmacol 13:3–9 (1991).
Westergaard, U. & Dietschy, J.M., J Clin Inves 58:97–108 (1976).
Wilson, M.D. & Rudel, L.L., J Lipid Res 35:943–955 (1994).
Compassi, S., et al., Biochem 34:16473–16482 (1995).
Fernley, H.N., in "The Enzymes" (Boyer, P.D., Ed.), vol. VI, pp. 417–447, Associated Press, NY (1971).
Gallo, L.L., et al., Proc Soc Exp Biol Med 156:277–281 (1977).
Ghosh, N.V., and Fishman, W.H., J Biol Chem 241:2516–2522 (1966).
Gylling, H. & Miettinen T.A., Atherosclerosis 117:305–308 (1995).
Hamilton, R.L., in "Plasma Secretion by the Liver" (Glaucman, H., et al., Eds.) p. 357, Associated Press, New York (1983).
Havel, R.J. & Kane, J.P., in "The Metabolic and Molecular Basis of Inherited Disease" (Scriver, C.R., et al., Eds.) pp. 1841–1851, McGraw–Hill, New York (1995).
Hoffman–Blume, E.G., et al., Eur J Biochem 199:305–312 (1991).
Ikeda, I., et al., J Lipid Res 29:1583–1591 (1988).
Lowe, M.E., et al., Biochem Biophys Acta 1037:170–177 (1990).
Mahmood, A., et al., J Clin Investig 93:70–80 (1994).
Metaye, T., et al., Biochem Pharmacol 37:4263–4268 (1988).

*Primary Examiner*—Kevin E. Weddington
*Attorney, Agent, or Firm*—Jaeckle Fleischmann & Mugel, LLP; Susan J. Braman, Esq.

[57] ABSTRACT

The present invention is directed to a method of inhibiting cholesterol transport through the intestinal lumen of a subject. The method comprises administering an intestinal alkaline phosphatase inhibitor to the subject. The inhibition of intestinal alkaline phosphatase prevents transport of exogenous cholesterol through the intestinal lumen and therefore decreases plasma levels of cholesterol. The invention further provides a method of screening for agents which inhibit cholesterol transport. This method comprises expressing intestinal alkaline phosphatase in a host cell, exposing the host cell to an agent and cholesterol, and determining whether the cholesterol is transported into the host cell. Since intestinal alkaline phosphatase mediates cholesterol transport into the cell, an agent that inhibits the expressed intestinal alkaline phosphatase (or inhibits the expression of intestinal alkaline phosphatase), will inhibit cholesterol transport.

2 Claims, 5 Drawing Sheets

METHOD OF INHIBITING CHOLESTEROL TRANSPORT

The subject matter of this application was made with support from the United States Government (National Institutes of Health Grant No. 2R37DK36112.

FIELD OF THE INVENTION

The present invention relates to a method of inhibiting cholesterol transport, and more particularly to a method of inhibiting cholesterol transport through the intestinal lumen of a subject by inhibiting intestinal alkaline phosphatase.

BACKGROUND OF THE INVENTION

Throughout this application various publications are referenced, many in parenthesis. Full citations for these publications are provided at the end of the Detailed Description. The disclosures of these publications in their entireties are hereby incorporated by reference in this application.

The cholesterol content of the plasma is important in the development of atherosclerotic disease, both with respect to the coronary arteries and heart attacks and the cerebral arteries and strokes. Plasma cholesterol is the result of both endogenous production of cholesterol in the liver and other tissues, and exogenous absorption of cholesterol from the intestine. Intestinal cholesterol is derived both from the diet and from entero-hepatic recirculation of cholesterol.

The cellular uptake of cholesterol from the plasma utilizes a pathway which is understood in broad outline. Cholesterol and cholesterol esters are present in lipoproteins circulating in the plasma. A receptor on the cell surface recognizes protein motifs in the lipoproteins, binds the lipoprotein, and internalizes the complex in a clathrin coated pit (Havel & Kane 1995).

In contrast, cholesterol transport from the intestinal lumen is poorly understood (Wilson & Rudel 1994). Exogenous cholesterol from the diet and enteric-hepatic recirculation is important in maintaining plasma cholesterol levels (Gylling & Miettinen 1995). The intestinal lumen does not contain lipoproteins, and so the pathway for the uptake of exogenous cholesterol in the intestine must be radically different from the pathway utilized for plasma cholesterol (Tso 1985).

Early models suggested that cholesterol was incorporated into the mucosal membrane by a physical process (Tso 1985) or a cholesterol exchange. Several more recent lines of data have implicated a receptor-like protein molecule on the intestinal surface that can mediate cholesterol absorption (Thurmhofer et al. 1991; Thurmhofer & Hauser 1990). The presence of a receptor explained the specificity of the uptake, since the enterocytes transported cholesterol eight to ten fold better than the chemically very similar plant steroid, sitosterol (Ikeda et al. 1988). Cholesterol is present in the gut lumen in mixed micelles with bile salts, so that the sterol can cross the unstirred water layer in a soluble form (Thomson 1980; Westergarde & Dietschy 1976). Cholesterol esters in the diet are hydrolyzed to the free alcohol by pancreatic esterase before absorption (Gallo et al. 1977). After crossing the membrane, the cholesterol is eventually localized in a nascent chylomicron in the smooth endoplasmic reticulum (Christensen et al. 1983) where the lipids combine with apolipoprotein B to begin the assembly of the chylomicron for export into the lymphatics (Hamilton 1983).

A protein possibly involved in the absorption of cholesterol ester from rabbit intestine has been reported (Compassi et al. 1995). The protein produced by autolysis was soluble without detergents and had polypeptides of 96 and 57k daltons.

Intestinal alkaline phosphatase (Fermby 1971) is a membrane bound, glycan inositol phosphate anchored protein (Hoffman-Blume et al. 1991) of unknown physiologic function. It is bound with the anchor as well as in a form without the anchor. It is anchored to the microvillus membrane via a glycosylphosphatidylinositol linkage and is found both intracellularly and intralumenally (Brasitos et al. 1988). The enzyme is released in combination with triglycerides in the form of "surfactant-like particles" associated with the enterocyte surface and in the Golgi regions (Blume-Hoffmann et al. 1991). These particles increase during fat feeding (Mahmood et al. 1994) and are believed to be precursors of nascent chylomicrons. At alkaline pH, intestinal alkaline phosphatase can hydrolyze a number of phosphorylated substrates. The phosphatase activity of the enzyme can be inhibited by levamisole (VanBelle 1976; Metaye et al. 1988). This anthelmintic and immune response modulating drug has been used for a number of medical indications, but its mode of action is not well understood (Metaye et al. 1988; Wavwe & Janssen 1991).

A need continues to exist for an effective method to control absorption of exogenous cholesterol, in order to reduce plasma levels of cholesterol thereby reducing the risk of atherosclerotic disease.

SUMMARY OF INVENTION

To this end, it is an object of the subject invention to provide a method of inhibiting cholesterol transport from the intestinal lumen of a subject. The method comprises administering an intestinal alkaline phosphatase inhibitor to the subject. The inhibition of intestinal alkaline phosphatase prevents transport of exogenous cholesterol through the intestinal lumen and therefore decreases plasma levels of cholesterol.

The invention further provides a method of screening for agents which inhibit cholesterol transport. This method comprises expressing intestinal alkaline phosphatase in a host cell, exposing the host cell to an agent and cholesterol, and determining whether the cholesterol is transported into the host cell. Since intestinal alkaline phosphatase mediates cholesterol transport into the cell, an agent that inhibits the expressed intestinal alkaline phosphatase (or inhibits the expression of intestinal alkaline phosphatase), will inhibit cholesterol transport.

BRIEF DESCRIPTION OF THE DRAWINGS

These and other features and advantages of this invention will be evident from the following detailed description of preferred embodiments when read in conjunction with the accompanying drawings in which.

DETAILED DESCRIPTION

Figure 1:
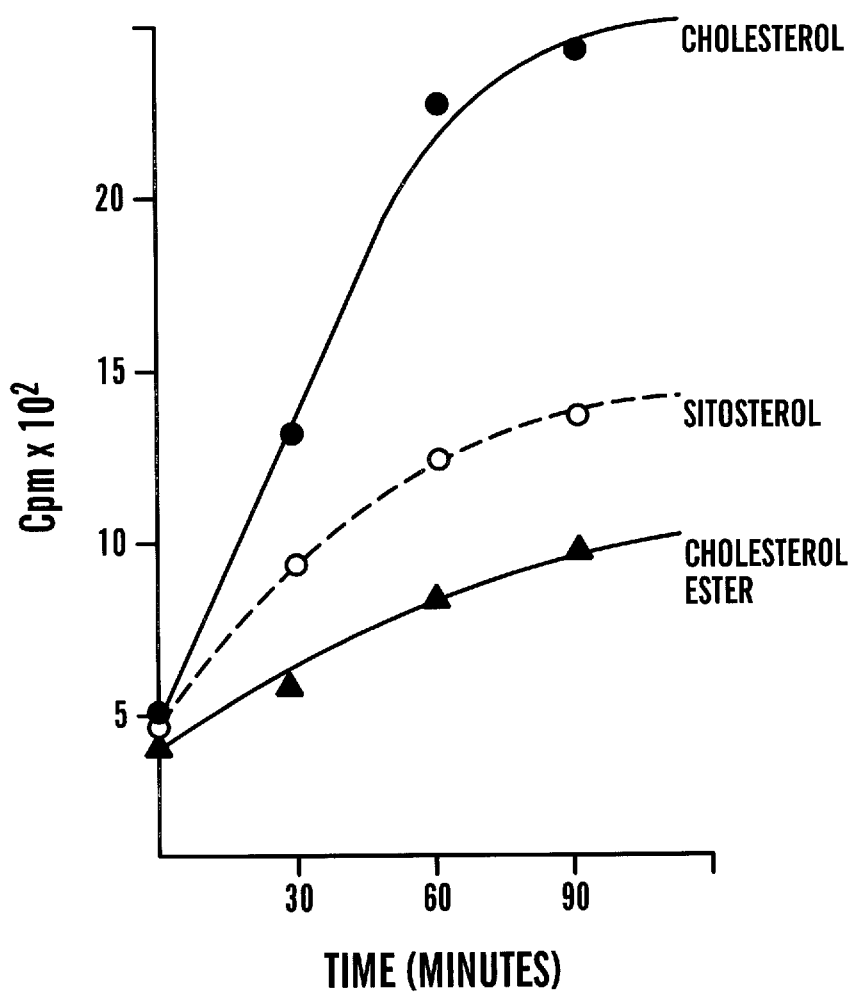
FIG. 1 illustrates the specific uptake of cholesterol from micelles by rat intestinal cells.

The subject invention provides a method of inhibiting cholesterol transport from the intestinal lumen of a subject into the body. The method comprises administering an effective amount of an intestinal alkaline phosphatase (IAP) inhibitor to the subject.

As used herein, suitable subjects include, for example, those which have not previously been diagnosed as having high plasma cholesterol levels, those which have previously been determined to be at risk of having high plasma cholesterol levels, and those who have been initially diagnosed as having high plasma cholesterol levels.

As further used herein, an intestinal alkaline phosphatase inhibitor refers to any compound capable of inhibiting intestinal alkaline phosphatase, either by interfering with the function of the intestinal alkaline phosphatase enzyme or by interfering with production of intestinal alkaline phosphatase. The IAP inhibitor can be a traditional chemical such as 2,3,5,6-tetrahydro-6-phenylimidazo-[2,1-b]thiazole ("tetramisole") or pharmaceutically acceptable salts thereof, with levamisole (the L-(-)-form of tetramisole) being presently preferred. Other forms of tetramisole can also be used (see Table 2 for listing of other forms and the company that distributes and/or manufactures the other forms).

Other traditional chemicals which are intestinal alkaline phosphatase inhibitors are cimetidine-like derivatives (Metaye, et al. 1988), including Doxantrazob, AA-344, M+B-22948m 121-79917, W-13560 (Schwender, et al. 1981), pyridal [2, 1–6] quinazolines (Schwender, et al. 1982), and many amino acids in particular L-phenylalanine (Gosh and Fishman 1966), and tannic acids derived from plants (Tebib, et al. 1995). A general discussion of such inhibitors can be found in Fermby 1971.

Alternatively, the inhibitor of intestinal alkaline phosphatase can be, for example, a nucleic acid molecule (which binds to a nucleic acid molecule encoding the intestinal alkaline phosphatase, preventing expression of the intestinal alkaline phosphatase), a peptide (which binds to the intestinal alkaline phosphatase, preventing binding of the cholesterol to the intestinal alkaline phosphatase), or an antibody (which binds to the intestinal alkaline phosphatase, preventing binding of the cholesterol to the intestinal alkaline phosphatase).

Suitable nucleic acid molecules include, for example, antisense nucleic acid molecules and ribozymes. Antisense nucleic acid molecules are complementary to at least a portion of the mRNA encoding the intestinal alkaline phosphatase (IAP). The nucleic acid and amino acid sequences of IAP are known. See, for example, Lowe et al. 1990. Antisense nucleic acid molecules can be RNA or single-stranded DNA, and can be complementary to the entire mRNA molecule encoding the IAP (i.e. of the same nucleotide length as the entire molecule). It may be desirable, however, to work with a shorter molecule. In this instance, the antisense molecule can be complementary to a portion of the entire mRNA molecule encoding the IAP. These shorter antisense molecules are capable of hybridizing to the mRNA encoding the entire molecule, and preferably consist of at least twenty nucleotides. These antisense molecules can be used to reduce levels of IAP, by introducing into cells an RNA or single-stranded DNA molecule that is complementary to at least a portion of the mRNA of the IAP (i.e. by introducing an antisense molecule). The antisense molecule can base-pair with the mRNA of the IAP, preventing translation of the mRNA into protein. Thus, an antisense molecule to the IAP can prevent translation of mRNA encoding the IAP into a functional IAP protein, thereby decreasing the transport of cholesterol into the cell by the IAP.

Antisense molecules can be introduced into cells by any suitable means. Suitable cells include epithelial absorptive cells which are the site of cholesterol absorption. In one embodiment, the antisense RNA molecule is injected directly into the cellular cytoplasm, where the RNA interferes with translation. A vector may also be used for introduction of the antisense molecule into a cell. Such vectors include various plasmid and viral vectors. For a general discussion of antisense molecules and their use, see Han et al. 1991 and Rossi 1995.

A special category of antisense RNA molecules, known as ribozymes, having recognition sequences complementary to specific regions of the mRNA encoding the IAP, can also be used as inhibitors. Ribozymes not only complex with target sequences via complementary antisense sequences but also catalyze the hydrolysis, or cleavage, of the template mRNA molecule.

Expression of a ribozyme in a cell can inhibit gene expression (such as the expression of the IAP). More particularly, a ribozyme having a recognition sequence complementary to a region of a mRNA encoding the IAP can be used to decrease expression of IAP. A cell with a first level of expression of IAP is selected, and then the ribozyme is introduced into the cell. The ribozyme in the cell decreases expression of IAP in the cell, because mRNA encoding the IAP is cleaved and cannot be translated.

Ribozymes can be introduced into cells by any suitable means. Suitable cells include epithelial absorptive cells of the intestinal lumen which are the site of cholesterol absorption. In one embodiment, the ribozyme is injected directly into the cellular cytoplasm, where the ribozyme cleaves the mRNA and thereby interferes with translation. A vector may be used for introduction of the ribozyme into a cell. Such vectors include various plasmid and viral vectors (note that the DNA encoding the ribozyme does not need to be "incorporated" into the genome of the host cell; it could be expressed in a host cell infected by a viral vector, with the vector expressing the ribozyme, for instance). For a general discussion of ribozymes and their use, see Sarver et al. 1990, Chrisey et al. 1991, Rossi et al. 1992, and Christoffersen et al. 1995.

The nucleic acid molecules which are inhibitors of IAP according to the subject invention can be expressed in suitable host cells using conventional techniques. Any suitable host and/or vector system can be used. For in vitro expression such as would be done with a screening method, bacterial hosts (for example, *Escherichia coli*) and mammalian hosts (for example, Hela cells, Cv-1 cells, COS cells) are preferred. For in vivo expression as a method of inhibiting cholesterol transport in a subject, the most suitable host cell is the intestinal lumen cell where cholesterol transport occurs.

As indicated, some of these methods of transforming a cell require the use of an intermediate plasmid vector. U.S. Pat. No. 4,237,224 to Cohen and Boyer describes the production of expression systems in the form of recombinant plasmids using restriction enzyme cleavage and ligation with DNA ligase. These recombinant plasmids are then introduced by means of transformation and replicated in unicellular cultures including procaryotic organisms and eucaryotic cells grown in tissue culture. The DNA sequences are cloned into the plasmid vector using standard cloning procedures known in the art, as described by Sambrook et al. (1989).

As indicated above, levels of IAP in a cell, such as an intestinal lumen cell, can be decreased by introducing an antisense or ribozyme construct into the cell. An antisense construct blocks translation of mRNA encoding IAP into the IAP enzyme. A ribozyme construct cleaves the mRNA encoding the IAP thus also preventing expression of functional IAP enzyme. For in vivo decreasing of expression of IAP, various gene therapy techniques can again be utilized to introduce the antisense or ribozyme construct into the desired cell. The construct may need to be targeted to the desired cells (i.e., the intestinal lumen cells) by known methods, since in other cells of the subject decreased expression of IAP may not be desired.

The transport of cholesterol by intestinal alkaline phosphatase can also be inhibited by blocking the action of IAP in the desired cell (such as an intestinal lumen cell) with inhibitors that are peptide drug products and/or small molecules (see generally, Bevan et al. 1995; Sepetov et al. 1995; O'Connor et al. 1994; Webber et al. 1993).

Drugs, such as peptide drugs, can be made using various methods known in the art. One such method utilizes the development of epitope libraries and biopanning of bacteriophage libraries. Briefly, attempts to define the binding sites for various monoclonal antibodies have led to the development of epitope libraries. Parmley and Smith developed a bacteriophage expression vector that could display foreign epitopes on its surface (Parmley and Smith 1988). This vector could be used to construct large collections of bacteriophage which could include virtually all possible sequences of a short (e.g. six-amino-acid) peptide. They also developed biopanning, which is a method for affinity-purifying phage displaying foreign epitopes using a specific antibody (see Parmley and Smith 1988; Cwirla et al. 1990; Scott and Smith 1990; Christian et al. 1992; Smith and Scott 1993).

After the development of epitope libraries, Smith et al. then suggested that it should be possible to use the bacteriophage expression vector and biopanning technique of Parmley and Smith to identify epitopes from all possible sequences of a given length. This led to the idea of identifying peptide ligands for antibodies by biopanning epitope libraries, which could then be used in vaccine design, epitope mapping, the identification of genes, and many other applications (Parmley and Smith 1988; Scott 1992).

Using epitope libraries and biopanning, researchers searching for epitope sequences found instead peptide sequences which mimicked the epitope, i.e., sequences which did not identify a continuous linear native sequence or necessarily occur at all within a natural protein sequence. These mimicking peptides are called mimotopes. In this manner, mimotopes of various binding sites/proteins have been found. LaRocca et al. (1992) expressed a mimotope of the human breast epithelial mucin tandem repeat in *Escherichia coli*. Balass et al. (1993) identified a hexapeptide that mimics a conformation-dependent binding site of the acetylcholine receptor. Hobart et al. (1993) isolated a mimotope that mimics the C6 epitope (the epitope for the sixth component of complement).

The sequences of these mimotopes, by definition, do not identify a continuous linear native sequence or necessarily occur in any way in a naturally-occurring molecule, i.e. a naturally occurring protein. The sequences of the mimotopes merely form a peptide which functionally mimics a binding site on a naturally-occurring protein. For example, the mimotope of Balass et al. (1993) mimics the binding site of the acetylcholine receptor.

Many of these mimotopes are short peptides. The availability of short peptides which can be readily synthesized in large amounts and which can mimic naturally-occurring sequences (i.e. binding sites) offers great potential application.

Using this technique, mimotopes to a monoclonal antibody that recognizes IAP can be identified. The sequences of these mimotopes represent short peptides which can then be used in various ways, for example as peptide drugs that bind to IAP and prevent the transport of cholesterol by IAP. Once the sequence of the mimotope is determined, the peptide drugs can be chemically synthesized.

The inhibitors of IAP, such as traditional chemicals and peptide drugs disclosed herein, may be administered alone or in combination with compatible carriers as a composition. Compatible carriers include suitable pharmaceutical carriers or diluents. The diluent or carrier ingredients should be selected so that they do not diminish the therapeutic effects of the proteins, fragments, or drugs used in the present invention.

The compositions herein may be made up in any suitable form appropriate for the desired use; e.g., oral, parenteral, or topical administration. Suitable dosage forms for oral use include tablets, dispersible powders, granules, capsules, suspensions, syrups, and elixirs. Inert diluents and carriers for tablets include, for example, calcium carbonate, sodium carbonate, lactose, and talc. Tablets may also contain granulating and disintegrating agents such as starch and alginic acid, binding agents such as starch, gelatin, and acacia, and lubricating agents such as magnesium stearate, stearic acid, and talc. Tablets may be uncoated or may be coated by known techniques to delay disintegration and absorption. Inert diluents and carriers which may be used in capsules include, for example, calcium carbonate, calcium phosphate, and kaolin. Suspensions, syrups, and elixirs may contain conventional excipients, for example, methyl cellulose, tragacanth, sodium alginate; wetting agents, such as lecithin and polyoxyethylene stearate; and preservatives, e.g., ethyl-p-hydroxybenzoate.

Dosage forms suitable for parenteral administration include solutions, suspensions, dispersions, emulsions, and the like. They may also be manufactured in the form of sterile solid compositions which can be dissolved or suspended in sterile injectable medium immediately before use. They may contain suspending or dispersing agents known in the art. Examples of parenteral administration are intraventricular, intracerebral, intramuscular, intravenous, intraperitoneal, rectal, and subcutaneous administration.

It will be appreciated that the actual preferred amount of inhibitor to be administered according to the present invention will vary according to the particular inhibitor, the particular composition formulated, and the mode of administration. Many factors that may modify the action of the inhibitor can be taken into account by those skilled in the art; e.g., body weight, sex, diet, time of administration, route of administration, rate of excretion, condition of the subject, drug combinations, and reaction sensitivities and severities. Administration can be carried out continuously or periodically within the maximum tolerated dose. Optimal administration rates for a given set of conditions can be ascertained by those skilled in the art using conventional dosage administration tests.

The invention further utilizes an inhibitor of intestinal alkaline phosphatase which is an antibody or fragment thereof specific for the IAP. The antibody binds to the IAP, preventing transport of cholesterol by IAP. Such antibodies include polyclonal antibodies and monoclonal antibodies capable of binding to the IAP, as well as fragments of these antibodies, and humanized forms. Humanized forms of the antibodies may be generated using one of the procedures known in the art such as chimerization. Fragments of the antibodies include, but are not limited to, the Fab, the Fab2, and the Fd fragments.

The monoclonal antibodies can be produced by hybridomas. A hybridoma is an immortalized cell line which is capable of secreting a specific monoclonal antibody.

In general, techniques for preparing polyclonal and monoclonal antibodies as well as hybridomas capable of producing the desired antibody are well known in the art (see Campbell 1984 and St. Groth et al. 1980). Any animal (mouse, rabbit, etc.) which is known to produce antibodies can be immunized with the antigenic IAP (or an antigenic fragment thereof). Methods for immunization are well known in the art. Such methods include subcutaneous or intraperitoneal injection of the enzyme. One skilled in the art will recognize that the amount of the enzyme used for immunization will vary based on the animal which is immunized, the antigenicity of the enzyme, and the site of injection.

The enzyme which is used as an immunogen may be modified or administered in an adjuvant in order to increase the enzyme's antigenicity. Methods of increasing the antigenicity of an enzyme (i.e., a protein) are well known in the art and include, but are not limited to, coupling the antigen with a heterologous protein (such as a globulin or beta-galactosidase) or through the inclusion of an adjuvant during immunization.

For monoclonal antibodies, spleen cells from the immunized animals are removed, fused with myeloma cells, such as SP2/O-Ag 15 myeloma cells, and allowed to become monoclonal antibody producing hybridoma cells.

Any one of a number of methods well known in the art can be used to identify the hybridoma cell which produces an antibody with the desired characteristics. These include screening the hybridomas with an ELISA assay, western blot analysis, or radioimmunoassay (Lutz et al. 1988).

Hybridomas secreting the desired antibodies are cloned and the class and subclass are determined using procedures known in the art (Campbell 1984).

For polyclonal antibodies, antibody containing antisera is isolated from the immunized animal and is screened for the presence of antibodies with the desired specificity using one of the above-described procedures.

It should be readily apparent to those skilled in the art that cholesterol transport can also be inhibited with any chemical, nucleic acid molecule, peptide, antibody, etc. that will bind to exogenous cholesterol and prevent its transport by IAP. As used herein, all references to inhibitors of IAP are intended to encompass such chemicals, nucleic acid molecules, peptides, antibodies, etc. since they are interfering with transport of cholesterol by IAP, i.e. they are inhibitors of IAP transport of cholesterol. For example, an IAP binding site on cholesterol could be blocked with a chemical, nucleic acid molecule, peptide, antibody, etc.

Having thus defined the numerous IAP inhibitors that can be used in the subject invention, the invention further provides a method of screening for agents which inhibit cholesterol transport. The method comprises expressing intestinal alkaline phosphatase in a host cell, exposing the host cell to an agent and cholesterol, and determining whether the cholesterol is transported into the host cell. The agent is an effective inhibitor of cholesterol transport if transportation of the cholesterol into the host cell is inhibited. The expression of intestinal alkaline phosphatase in a host cell can be due to the presence of an endogenous intestinal alkaline phosphatase gene in a host cell (i.e. the cell naturally expresses intestinal alkaline phosphatase) or can be due to the presence of a heterologous intestinal alkaline phosphatase gene in a host cell (i.e. the cell does not naturally express intestinal alkaline phosphatase or expresses it at low levels, and the cell is transformed with heterologous nucleic acid encoding IAP in order to express intestinal alkaline phosphatase). Preferably, the cholesterol to which the cell is exposed has been labeled with a detectable marker. This allows for ready detection of transport of the cholesterol into the host cell. Suitable labels are known in the art and include, for example, a radioactive isotope, biotin, an element opaque to X-rays, or a paramagnetic ion. Radioactive isotopes are commonly used and are well known to those skilled in the art. Representative examples include C-14 and H-3. Biotin is a standard label which would allow detection of the biotin labeled cholesterol with avidin. When using such labels, the labeled cholesterol can be imaged using methods known to those skilled in the art. Such imaging methods include, but are not limited to, X-ray, CAT scan, PET scan, NMRI, and fluoroscopy. Other suitable labels include enzymatic labels (such as horseradish peroxidase) and fluorescent labels (such as FITC or rhodamine, etc.).

EXAMPLE I

IDENTIFICATION OF CHOLESTEROL TRANSPORT PROTEIN

Any protein involved in the passage of cholesterol from the gut lumen to the nascent chylomicron would be expected to have certain specific properties. These are:

(1) It should be membrane bound in contrast to the nascent chylomicron which would "float" during centrifugation.

(2) It would have non-esterified cholesterol bound to it, indicating a step in the pathway prior to the formation of nascent chylomicrons.

(3) It would demonstrate ligand specificity, i.e. it would not bind sitosterol.

(4) It would not contain a protein corresponding to apolipoprotein B48.

(5) It would bind cholesterol.

It was an object of the subject invention to isolate such a protein from rat intestinal mucosal homogenates. A protein was isolated from rat duodenal mucosa that has these characteristics.

Fifty Wistar male rats were anesthetized with phenobarbital and a celiotomy was performed. The duodenum was isolated with ligatures of umbilical tape at the pylorus and the ligament of Treitz. One ml of a suspension of micelles containing $^3$H-cholesterol and $^{14}$C-sitosterol together with taurodeoxycholate (TDC) and dimyristic phosphatidyl choline (DMPC) (Safonova et al. 1994) were injected into the isolated duodenum of each rat. Following ten minutes incubation in the duodenum the gut loop was excised. The duodenum was opened lengthwise with iris scissors and mucosal contents were vigorously washed in two changes of 0.15M NaCl, 20 mM Hepes solution (pH 7.5). The mucosa was scraped free with a glass microscope slide and homogenized in a Virtis homogenizer for 5 minutes and 12 strokes in a Potter-Elvehjeim homogenizer as previously described (Conrad et al. 1993). Total uptake into the homogenate was 16% of the added cholesterol and 2% of sitosterol, demonstrating greater specificity for the cholesterol. Membranes were collected by centrifugation at 20,000×g for 20 minutes. Membrane proteins were extracted overnight at 4° C. in 1% Triton X 100 20 mM Hepes pH 7.5. The suspension was centrifuged at 20,000×g for 20 minutes. The solubilized material (70 ml) contained 70% of the radiolabeled cholesterol. The solubilized material was applied to a 240 ml column of DE-92 (Whatmann) equilibrated in 20 mM Hepes, 1% Triton X 100 pH 7.5 and eluted with a saline gradient. The radioactive material was pooled, the pH adjusted to pH 5.5 and applied to a 80 ml column of CM cellulose equilibrated with 20 mM Hepes pH 5.5 1% Triton X 100 and eluted with a buffered saline gradient (pH 7.5). The radioactive material was pooled and absorbed on hydroxyapatite (Biorad, Richmond, N.Y.). The precipitated resin was washed extensively with 10 mM Hepes 10 mM NaCl pH 7.5 and eluted with successive washes of 1M NaCl 20 mM Hepes pH 5.5 1% Triton X 100. A purification of approximately 130 fold was obtained, although this may be an underestimate because cholesterol continuously dissociates from the protein. Approximately 1 mg of protein was obtained.

Cholesterol binding protein from rat intestine:

The protein fraction isolated retained the $^3$H-cholesterol bound to the protein but no $^{14}$C-sitosterol was detected. SDS-PAGE of the protein revealed a single major band of approximately 100,000 daltons. No band corresponding to the known molecular size of apolipoprotein B48 was detected. Microsequence of the N-terminus of the protein showed a high degree of homology to intestinal alkaline phosphatase as shown in Table 1.

Approximately 50 μg of protein was precipitated from the purified preparation with 80% ethanol at 4° C. overnight, and collected by centrifugation in a microfuge. This was resuspended in 20 μg of SDS sample buffer and electrophoresed after heating on a 7.5% acrylamide SDS gel according to the method of Laemmli (Laemmli 1970) and stained with Coomassie blue. The size of the polypeptide was compared to known standards. A similar sample was transblotted to Immobilin Transfer membrane (Millipore, Bedford, MA) and stained with Coomassie blue. This was subjected to microsequence analysis and compared to known protein sequences (see Table 1). Sequence analysis was performed using an Applied Biosystems Model 475A sequencer.

Cholesterol was present in the non-esterified form:

Extraction of the purified protein with organic solvents released all the bound radioactivity. Subsequent chromatography and thin layer chromatography (TLC) demonstrated that the cholesterol present on the protein was in the non-esterified form. A protein solution eluted from hydroxyapatite containing 0.85 mg of protein in 70 ml of buffer was concentrated on Amicron PM10 membrane to 7 cc and precipitated with 80% ethanol. All the radioactivity remained in the ethanol. This was evaporated to dryness and extracted with 2 ml of H$_2$O, 2 ml methanol and 4 ml of CHCl$_3$. The chloroform layer was washed twice with water, evaporated to dryness and resuspended in 1 ml of chloroform. An aliquot of 100 microliters was applied to a 20×20 cm silica TLC plate (Fisher Scientific). The plate was developed in hexane:ether 100:20. After drying 1 cm bands were scraped and counted with Beckman Ready-Safe scintillation fluid in a Beckman beta-counter. Radioactivity was detected corresponding only to the migration of unesterified cholesterol, and no activity co-migrated with the cholesterol ester.

Immunoprecipitation and rebinding of cholesterol by the isolated protein:

Antibody to alkaline phosphatase specifically precipitated $^3$H-cholesterol bound to the protein. Addition of $^3$H-cholesterol containing micelles prior to the addition of antibody to intestinal alkaline phosphatase increased the radioactivity in the immunoprecipitates (but not the controls without protein) showing that the isolated protein could rebind cholesterol. Non-specific antibody did not immunoprecipitate significant amounts of radioactive cholesterol. One ml of purified protein (0.85 μg/ml) in 1% Triton X-100 was incubated with increasing concentrations of $^3$H-cholesterol in the form of DMPC-taurodeoxycholate micelles. After 10 minutes at room temperature, 2.5 μl of antibody to human placental alkaline phosphatase (Accurate, Westbury, N.Y., AXL391) was added and the incubation continued at 4° C. for 4 hours. Sepharose-4-Protein G beads (Pharmacia) (10 μl) were added and incubated overnight at 4° C. The beads were collected in a microcentrifuge for 10 minutes, washed 3 times in 10 mM Hepes 10 mM CaCl$_2$ pH 7.5, resuspended in 1 ml of water and counted in a beta-scintillation counter. The cpm in the immunoprecipitate was determined with alkaline phosphatase specific antibody and a non-specific antisera (rabbit anti-goat IgG).

Increasing the cholesterol content of membranes in rat intestine microvillus membranes specifically decreased alkaline phosphatase activity but did not alter sucrase, maltase or lactase activities.

A membrane protein was thus isolated from rat duodenum that was labeled by cholesterol prior to the esterification step, suggesting its involvement in an early stage of cholesterol absorption. This protein has a sequence homology to intestinal alkaline phosphatase. It has an apparent molecular mass of 100 kDa on SDS-PAGE gels, binds radiolabeled cholesterol and is immunoprecipitated by commercial antibodies raised against intestinal alkaline phosphatase. This data presents support for a role of alkaline phosphatase in the transport of cholesterol across the mucosal cell membrane prior to association with the nascent chylomicron.

EXAMPLE II

INHIBITION OF ALKALINE PHOSPHATASE MEDIATED TRANSPORT OF CHOLESTEROL:

As shown in Example I, mucosal cholesterol transport involves a lumenal receptor-like protein which has been identified as homologous to intestinal alkaline phosphatase. Levamisole is known to be an inhibitor of alkaline phosphatase. Treatment of a rat intestinal cell line with Levamisole inhibited the uptake of cholesterol from micelles. The cholesterol accumulated on the plasma membrane of the treated cells, which were blocked in the transfer of cholesterol from the membrane to intracytoplasmic vesicles. This exemplifies a novel method of decreasing absorption of cholesterol.

Cholesterol transport:

Radioisotopes were obtained from NEN (Billerca, Mass.) and other chemicals from Sigma (St. Louis, Mo.). $^3$H-cholesterol micelles were prepared from dimyristic phosphatidyl choline (DMPC) and taurodeoxycholate (TDC) as described by others (Safanova et al. 1994). The final solution contained $2.2 \times 10^6$ cpm/ml, 0.1 μM cholesterol, 60 mM DMPC and 6.5 mM TDC. Micelles with $^{14}$C-sitosterol or $^3$H-cholesteryl oleate were similarly prepared using the appropriate steroid and had the same specific activity. IEC-6 cells (Quaroni et al. 1979) obtained from the American Type Culture Collection (12301 Parklawn Drive, Rockville, Md.) were grown to confluence on 12-well Corning tissue culture plates. The media was removed and the monolayers were washed with phosphate buffered saline containing calcium, magnesium, and glucose (PBS). One ml of PBS was added to each well and 40 μl of the micellar solution (for a final steroid concentration of 4 nM). After incubation at 37° C., the plates were chilled and the wells washed four times in cold PBS. Water (0.5 ml) was added, and the plates were sonicated for 15 minutes (Branson model B-220, Shelton, Conn.) and then washed in an additional 0.5 ml of water. The water lysates were combined and counted in Ready-Safe (Beckman, Fullerton, Calif.) scintillation fluid. There was less than 15% variation between duplicates. Under these conditions of incubation the monolayer remained intact.

Sucrose gradient separation:

Two petri dishes (7.5 cm) with monolayers of IEC-6 cells were grown to confluence and used for each experiment. Each plate was washed in PBS and then incubated with 3 ml of PBS containing 120 μl of cholesterol micelles. In two parallel petri dishes an identical incubation was performed but with the addition of 32 mM levamisole. After 60 minutes incubation the dishes were chilled, washed four times with cold PBS and then harvested by scraping the dishes into 8 ml of 10 mM Hepes, 10 mM NaCl pH 7.4. The cells were homogenized using a Tissue-Tearor (Biospec Products, Bartlettsville, Okla.) at full speed for 30 seconds×3. The homogenate was layered on top of a 26 ml linear sucrose gradient from 20–60% (w/w). Centrifugation was performed over 18–20 hours at 19,000 rpm with a S-20 rotor in a Sorvall RC28S (DuPont, Wilmington, Del.) centrifuge. The tubes were punched from the bottom and 1 ml fractions collected. Standard methods were used to identify the membrane fractions (Storrie & Madden 1990) utilizing p-nitrophenyl-sugars and spectrophotometric analysis.

Specific cholesterol uptake by IEC-6 cells:

Referring to FIG. 1, monolayers on 12 well plates of IEC-6 cells were incubated for the indicated times at 37° C. with $^3$H-cholesterol (●), $^{14}$C-sitosterol (o), or $^3$H-cholesteryl oleate (▲) in TDC-DMPC micelles as described above. The concentration (75 μM) and specific activity of the steroid was the same in all three conditions. After the desired incubation period, the media was removed, the monolayers were washed, the cells solubilized, and the amount of radioactivity incorporated into the cells was determined and plotted as counts per minute in the cells. The uptake of cholesterol was linear for at least an hour (FIG. 1). Sitosterol, a poorly absorbed plant sterol with chemical properties similar to cholesterol, was incorporated much less efficiently. At 60 minutes the cholesterol content of the cells was 2.7 times the sitosterol. Since sitosterol is closely related to cholesterol both chemically and physically, this indicated a biologically specific uptake. Cholesterol ester was also poorly absorbed by IEC-6 cells in the absence of added exogenous pancreatic cholesterol esterase. Thus, the IEC-6 cells were able to absorb specifically cholesterol from the mixed micelles.

Figure 2:
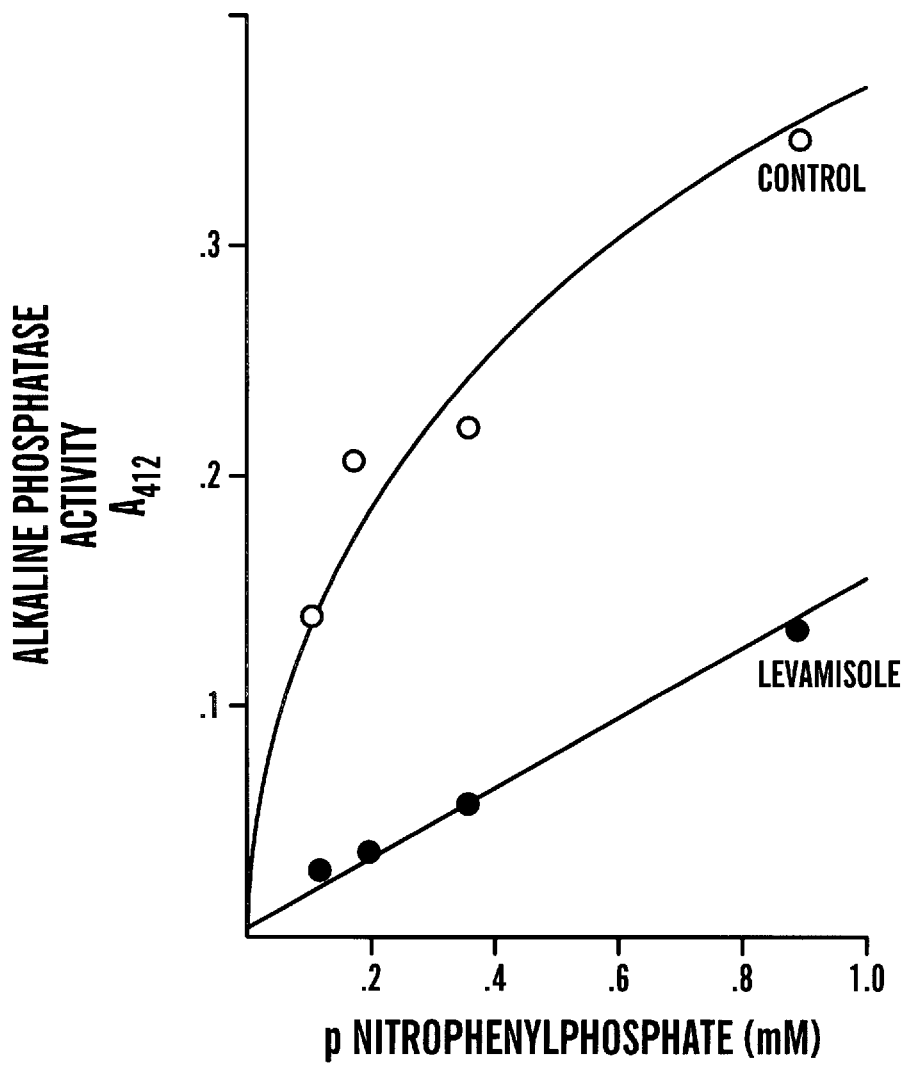
FIG. 2 illustrates the inhibition of alkaline phosphatase by levamisole.

Inhibition of alkaline phosphatase by levamisole:

Referring to FIG. 2, homogenates of IEC-6 cells were prepared and demonstrated the presence of a classic alkaline phosphatase activity. An incubation mixture of 0.55 ml was prepared containing 0.1 ml of 500 mM Hepes pH 8.5, 25 mM $MgCl_2$, 2.5 μM $ZnCl_2$, and 0.5 ml of homogenate [1.0 mg/ml protein as determined by BCA method (Pierce, Rockford, Ill.)]. The indicated amount of p-nitrophenyl phosphate was added and the incubation allowed to proceed for 30 minutes at 37° C. To some of the tubes levamisole (58 mM) was added. After the incubation the absorption at 412 nm was determined. At ph 8.5 (FIG. 2) alkaline phosphatase activity was competitively inhibited by levamisole. As is the case for other intestinal alkaline phosphatases (Metaye et al. 1988), relatively high concentrations of levamisole (58 mM) were required to inhibit the enzymatic activity.

Figure 3:
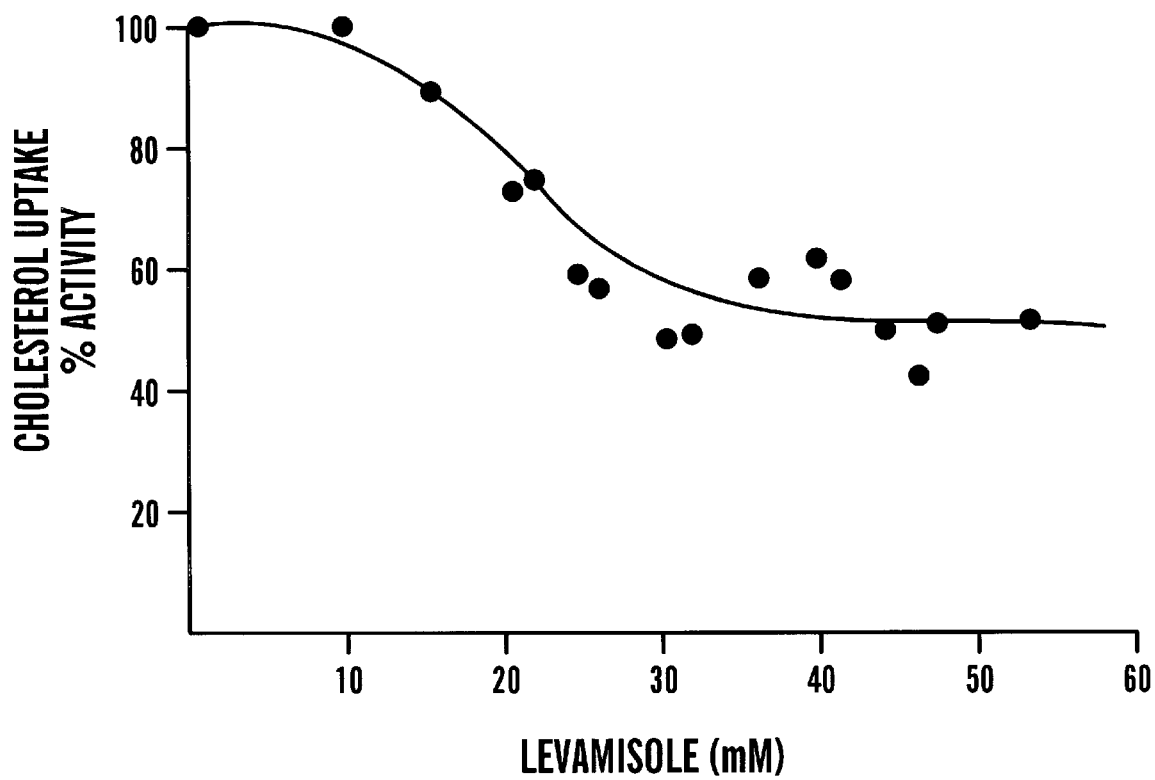
FIG. 3 illustrates the inhibition of cholesterol uptake by levamisole.

Inhibition of cholesterol absorption by levamisole:

Referring to FIG. 3, IEC-6 cells were incubated with $^3$H-cholesterol containing micelles and increasing concentrations of levamisole. The incubation was allowed to proceed at 37° C. for 30 minutes. Approximately 50% of the cholesterol uptake could be inhibited by levamisole. Increasing the concentrations of the drug did not result in complete inhibition of uptake (FIG. 3).

Figure 4:
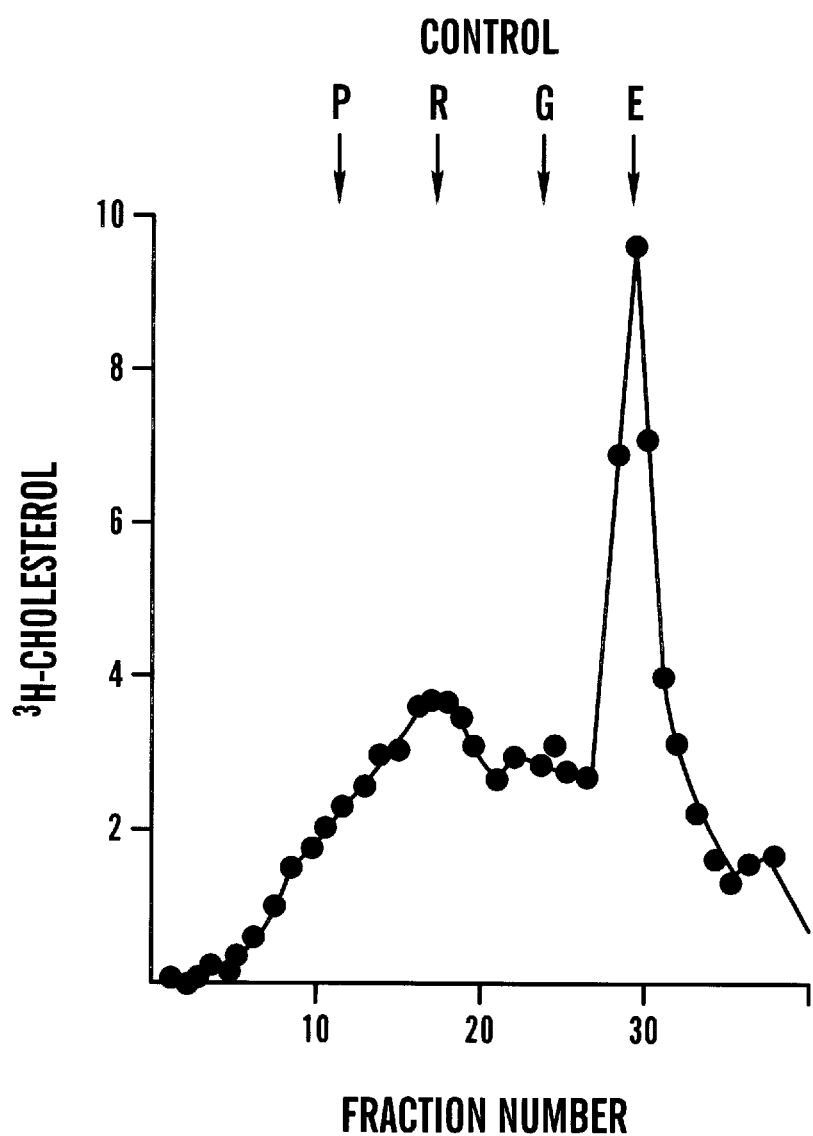
FIG. 4 illustrates the subcellular distribution of incorporated cholesterol.
Figure 5:
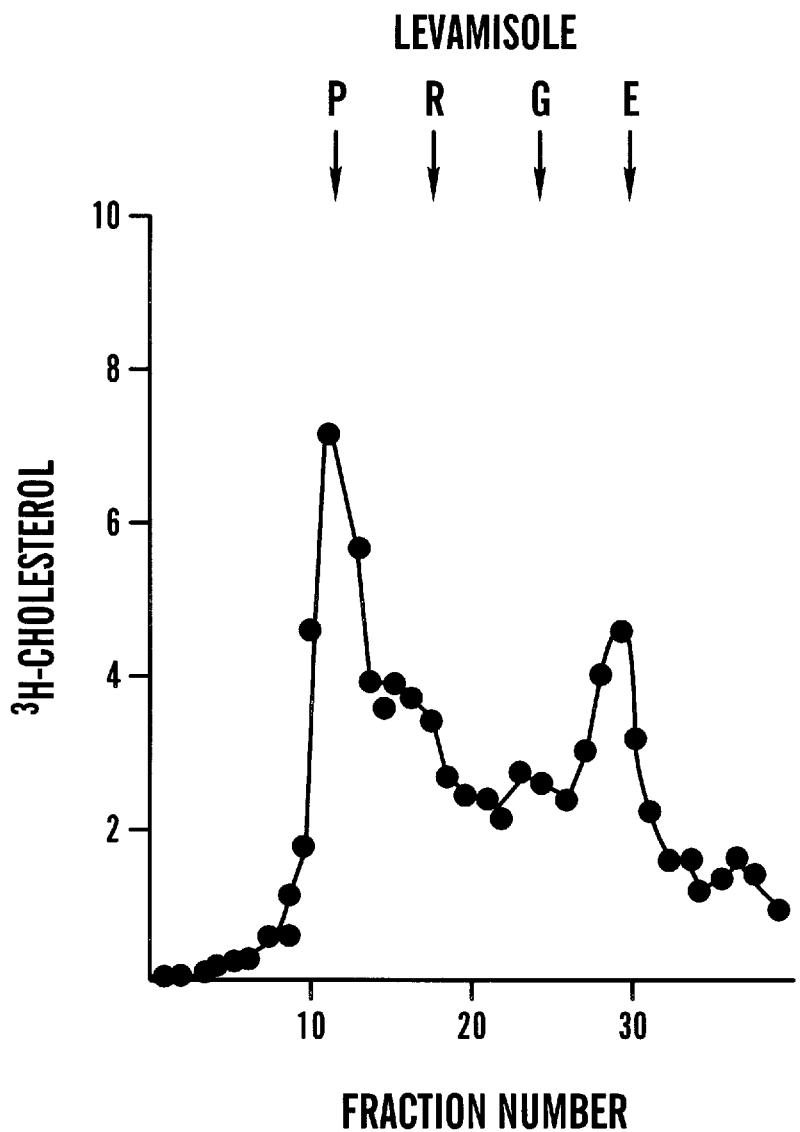
FIG. 5 illustrates the subcellular distribution of cholesterol after administration of levamisole.

Inhibition of cholesterol transit between membrane and vesicles:

Referring to FIG. 4, IEC-6 cells were incubated with $^3$H-cholesterol micelles for 60 minutes at 37° C., and then washed, homogenized, and separated on 20–60% sucrose gradients. The gradients were centrifuged to equilibrium. The location of various membrane fragments was determined by standard enzymatic methods (Storrie & Madden 1990). The fractions were identified as plasma membrane-like (P), rough endoplasmic reticulum-like (R), Golgi-like (G), endosome-like (E). The fraction containing the largest peak of radioactive cholesterol, the endosome-like fraction (E), was enriched for both lysosomal enzymes (β-hexosaminadase) and endoplasmic reticulum enzymes (α-glucosidase (Brada & Duback 1984)) and so contains a mixture of vesicle types. No distinct peak of radioactivity was observed in the plasma membrane-like fractions (P) in the absence of inhibitor. The highest density sucrose was at fraction 1, and the cytoplasmic (i.e. no sucrose) fraction began at fraction 30. When the cells were incubated with 32 mM levamisole, as well as $^3$H-cholesterol micelles, a different pattern emerged. The majority of the label was found in the plasma membrane fraction (P) and there was a decrease in the label seen in the endosome (E) fractions (FIG. 5). The addition of levamisole thus inhibited overall uptake of cholesterol from micelles in the intestinal cells. Blocking the uptake by levamisole resulted in accumulation in the plasma membrane fractions.

Pursuing the intestinal receptor mechanism, a protein labeled by cholesterol during the in vivo uptake of cholesterol in the rat intestine was isolated. This protein was labeled at an early step in the uptake of cholesterol, as demonstrated by the short incubation, the localization on the microvillus membrane, and the absence of esterification of the cholesterol. The protein was purified and demonstrated to be highly homologous to intestinal alkaline phosphatase.

The observation that a well-known enzyme like alkaline phosphatase might mediate cholesterol absorption was unexpected. But several characteristics of alkaline phosphatase were consistent with such a role. Alkaline phosphatase has an unknown physiologic function, and the observed phosphatase activity is virtually inactive at physiologic pH. Alkaline phosphatase is a membrane-bound protein, bound to the microvillus membrane by a glycan-inositol-phosphate anchor. Alkaline phosphatase can be released into the lumenal space of the intestine (Sossman et al. 1989). Furthermore, alkaline phosphatase has been associated with the process of neutral fat absorption (Zhang et al. 1996) in the formation of surfactant-like particles (SLP).

If cholesterol transport in the intestine was mediated by alkaline phosphatase, inhibitors of alkaline phosphatase might inhibit cholesterol transport. Levamisole, an antihelmithic and immune modulator, has been described as a specific inhibitor of alkaline phosphatase from a number of sources (Metaye et al. 1988; Wavwe & Janssen 1991). This drug inhibited the alkaline phosphatase identified in a rat intestinal cell line, IEC-6, and inhibited specific cholesterol uptake in the cells. The block induced by levamisole was between the plasma membrane and the vesicular compartment.

In the presence of levamisole the cholesterol was found on the plasma membrane fraction of the cell. The cholesterol in this fraction was so rapidly taken up into the cytoplasmic vesicles, that in the untreated cells only minimal labeling was detected, and the majority of the cholesterol was found in the vesicles inside the cells. This provided further evidence for a central role of the alkaline phosphatase in the absorption of cholesterol from mixed micelles.

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the claims which follow.

TABLE 1

| Isolated Protein | P | V | E | E | D | S | P | A | N | SEQ ID NO:1 |
|---|---|---|---|---|---|---|---|---|---|---|
|  | \| | \| | \| | \| | : | : | \| | \| | : |  |
| IAP-M | P | V | E | E | E | N | P | A | F | SEQ ID NO:2 |
| EAP-M | P | V | E | E | E | N | P | A | F | SEQ ID NO:2 |
| IAP-B | P | V | E | E | E | N | P | A | F | SEQ ID NO:2 |
| AP-R | P | V | E | E | E | N | P | A | F | SEQ ID NO:2 |

IAP-M: intestinal alkaline phosphatase (mouse)
EAP-M: embryonic precursor-alkaline phosphatase (mouse)
IAP-B: intestinal alkaline phosphatase (bovine)
AP-R: alkaline phosphatase (rat)

TABLE 2

| Drug | Company | Reference |
|---|---|---|
| Kentrax | ICI, Eire | 27:247 |
| R12546 | Janssen, Beerse, Belgium | MD p 116 * |
| Levasole | American Cyanamid, Prinator, N.J. | 27:40G 26:113D |
| Nemicide | ICI, Cheshire, UK | 21:156D |
| Stimamtol | Johnson & Johnson, Sao, Paulo | 30:158A |
| Tramisole Worm-chek | Ralston Purina, St. Louis | 24:921 |
| Dexamisole | Janssen, Beerse, Belgium | 26:36D |
| R12563 | Janssen, Beerse, Belgium | 26:36D |
| Bayer 9051 McN-Jr 8299 Citarin | McNeil | 18:114C |
| R8299 Citarin | McNeil | 18:114C |
| Anthelvet | Vetco | 18:51A |
| Citarin | McNeil | 18:114I |
| Nilvern | ICI, UK | 18:114C |
| Orovermal | Keto-Vemaco, Sao Paulo | 21:24N |
| Ripercol Spartakor | Janssen | 18:114I |
| Cyverm | Cyanamid, Gosport, New Hampshire | 35:70M |
| Decaris | Richter, Budapest | 24:6C |
| Evgamisole | Janssen, Beerse, Belgium | 31:56D |
| Levafas | Norbrook, Godalminy, Surrey | 39:1958 |
| Levovermax | Kutan, Opopharm, Zurick | 38:195E |
| Meglum | Bago, Buenos Aires | 30:156j |
| Nilvax 3i | ICI, Macclesfield, Cheshire | 35:11i |

TABLE 2-continued

| Drug | Company | Reference |
|---|---|---|
| Niratic | VMG Veteria Med Bad Oldesloe | 33:42P |
| Naratic-Puron | VMG Veterin Med. Bad Oldesloe | 33:27K |
| Solaskil | Specia, Paris | 24:265 |
| Totalon | Pitman-Moore, Washington Crossing, NJ | 39:138b |
| S/NSC 177023 | NCI Bethesda, MD & Lederie, Pearl Run River, NJ | 22:68D |
| S/R 12564 | Janssen, Beerse, Belgium | 22:67G |
| Levoripercal | Lundbeck, Copenhagen | 23:16T |
| Spectril 2 | ICI, Macclesfield, Cheshire | 33:196G |
| Belamisol | Bela-Pharm, Vechta | 37:131T |
| Levasol | Ceva, Watford, Harts | 35:1430 |
| Cyronomintic | Virbac, Zollikan | 41:1080 |
| Duphamisole | Dophar, Southampton | 36:139M |
| Immunol | Sanm, Rome | 35:41Q |
| Levacide | Norbrook, London | 36:87K |
| Levadin | Univetz, Bicester, Oxon | 35:146M |
| Levacide-C | Norbrook, Godalming, Surrey | 37:14C |
| Levazett | TZ-Arzneim Luding Lausen | 36:214D |
| Nematovet | Phar-vet, Billerbeck | 38:21B |
| Vetamisol | TAD Pharmazeut Werk, Luxhaven | 37:137F |

All references* to the journal "Unlisted Drugs", volume and page number, published by, Pharmaco Medical Documentations, Chatham, NJ 07928.
*MD p 116 is a reference to Martindale: The Extra Pharmacopoeia, 31st ed., ed. J.E.E. Reynolds, Royal Pharmaceutical Society, London (1996).

LIST OF REFERENCES CITED

Balass, M., et al., Proc Natl Acad Sci USA 90:10638–10642 (1993).
Bevan, P., et al., Trends in Biotechnology 13(3):115–121 (1995).
Blume-Hoffmann, E., et al., Eur J Biochem 199:305–312 (1991).
Brada, D. & Duback, V. C., Eur J Biochem 141:149–156 (1984).
Brasitos, T. A., et al., J Biol Chem 263:8592–8597 (1988).
Campbell, A. M., "Monoclonal Antibody Technology: Laboratory Techniques in Biochemistry and Molecular Biology", Elsevier Science Publishers, Amsterdam, The Netherlands (1984).
Christensen, N. J., et al., J Lipid Res 24:1229–1242 (1983).
Chrisey, L., et al., Antisense Research and Development 1 (1): 57–63 (1991)
Christian, R. B., et al., J Mol Biol 227:711–718 (1992).
Christoffersen, R. E. & Marr, J.J., Journal of Medicinal Chemistry 38(12):2023–2037 (1995).
Compassi, S., et al., Biochem 34:16473–16482 (1995).
Conrad, M. E., et al., Blood 81:517–521 (1993).
Cwirla, S. E., et al., Proc Natl Acad Sci USA 87:6378–6382 (1990).
Fermby, H. N., in "The Enzymes" (Boyer, P. D., Ed.), vol. VI, pp 417–447, Associated Press, New York (1971).
Gallo, L. L., et al., Proc Soc Exp Biol Med 156:277–281 (1977).
Gosh, N. V., and Fishman, W.H., J Biol Chem 241:2516–2522 (1966). Gylling, H. & Miettinem, T. A., Atherosclerosis 117:305–308 (1995).
Hamilton, R. L., in "Plasma Secretion by the Liver" (Glaucman, H., et al., Eds.) pp 357, Associated Press, New York (1983).

Han, L., et al., Proc Natl Acad Sci USA 88:4313–4317 (1991).
Havel, R. J. & Kane, J. P., in "The Metabolic and Molecular Basis of Inherited Disease" (Scriver, C. R., et al., Eds.) pp 1841–1851, McGraw-Hill, New York (1995).
Hobart, M. J., et al., Proc R Soc London B 252:157–162 (1993).
Hoffmann-Blume, E. G., et al., Eur J Biochem 199:305–312 (1991).
Ikeda, I., et al., J Lipid Res 29:1583–1591 (1988).
Laemmli, O. K., Nature 227:680–685 (1970).
LaRocca, D., et al., Hybridoma 11:191–201 (1992).
Lowe, M. E., et al., Biochem Biophys Acta 1037:170–177 (1990).
Lutz, et al., Exp Cell Res 175:109–124 (1988).
Mahmood, A., et al., J Clin Investig 93:70–80 (1994).
Metaye, T., et al., Biochem Pharmacol 37:4263–4268 (1988).
O'Connor, B., et al., Cancer Chemother Pharmacol 34:225–229 (1994).
Parmley, S. F. & Smith, G. P., Gene 73:305–318 (1988).
Quaroni, A., et al., J Cell Biol 80:248–265 (1979).
Rossi, J. J., British Medical Bulletin 51(1):217–225 (1995).
Rossi, J. J., et al., AIDS Research and Human Retroviruses 8(2):183–189 (1992).
Safonova, I. G., et al., Biochim Biophys Acta 1210:181–186 (1994).
Sambrook et al., "Molecular Cloning: A Laboratory Manual", 2d Edition, Cold Spring Harbor Laboratory Press, Cold Spring Harbor, N.Y. (1989).
Sarver, N., et al., Science 247:1222–1225 (1990).
Schwender, C. F., et al. Biochem Pharmacol 30:217–222 (1981).
Schwender, C. F., et al., J Med Chem 25:742–745 (1982).
Scott, J. K., Trends in Biochem Sci 17:241–245 (1992).
Scott, J. K. & Smith, G.P., Science 249:386–390 (1990).
Sepetov, N. F., et al., Proc Natl Acad Sci USA 92:5426–5430 (1995).
Smith, G. P. & Scott, J. K., Methods in Enzymology 217:228–257 (1993).
Sossman, N. L., et al., Am J Physiol 257:G14–G23 (1989).
St. Groth, et al., J Immunol Methods 35:1–21 (1980).
Storrie, B. & Madden, E. A., Methods Enz 182:203–225 (1990).
Tebib, K., et al., Enzymes & Proteins 48:51–60 (1995).
Thomson, A. B. R., J Lipid Res 21:1097–1107 (1980).
Thurmhofer, H. & Hauser, H., Biochem 29:2142–2148 (1990).
Thurmhofer, H., et al., Biochima et Biophysica Acta 1064:275–286 (1991).
Tso, P., Adv Lipid Res 21:143–186 (1985).
VanBelle, H., Clin Chem 22:972–976 (1976).
Wavwe, J. V. & Janssen, P. A., Int J Immunopharmacol 13:3–9 (1991).
Webber, G., et al., J Med Chem 36:733–746 (1993).
Westergarde, U. & Dietschy, J. M., J Clin Inves 58:97–108 (1976).
Wilson, M. D. & Rudel, L. L., J Lipid Res 35:943–955 (1994).
Zhang, Y., et al., Gastroenterology 110:478–488 (1996).

What is claimed is:

1. A method of inhibiting cholesterol transport from the intestinal lumen of a subject, said method comprising administering an intestinal alkaline phosphatase inhibitor to the subject.

2. The method of claim 1 wherein said intestinal alkaline phosphatase inhibitor is 2,3,5,G-tetrahydro-6-phenylimidazo-[2,1-b]thiazole.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 9 amino acids
        ( B ) TYPE: amino acid
        ( C ) STRANDEDNESS: Not Relevant
        ( D ) TOPOLOGY: linear ( i i ) MOLECULE TYPE: peptide ( x i ) SEQUENCE DESCRIPTION: SEQ ID NO:1:

Pro  Val  Glu  Glu  Asp  Ser  Pro  Ala  Asn
    1                        5

( 2 ) INFORMATION FOR SEQ ID NO:2:

( i ) SEQUENCE CHARACTERISTICS:
        ( A ) LENGTH: 9 amino acids
        ( B ) TYPE: amino acid
        ( C ) STRANDEDNESS: Not Relevant
        ( D ) TOPOLOGY: linear ( i i ) MOLECULE TYPE: peptide ( x i ) SEQUENCE DESCRIPTION: SEQ ID NO:2:

Pro  Val  Glu  Glu  Glu  Asn  Pro  Ala  Phe
    1                        5